United States Patent [19]

West et al.

[11] Patent Number: 5,486,598
[45] Date of Patent: Jan. 23, 1996

[54] SILICA MEDIATED SYNTHESIS OF PEPTIDES

[75] Inventors: Jon K. West; Larry L. Hench, both of Gainesville, Fla.

[73] Assignee: University of Florida, Gainsville, Fla.

[21] Appl. No.: 246,827

[22] Filed: May 20, 1994

[51] Int. Cl.⁶ .............................. B01J 21/06; C07K 1/02; C07K 1/10
[52] U.S. Cl. .................... 530/338; 204/157.82; 502/232; 502/233; 530/339; 562/561
[58] Field of Search .................................... 530/333, 338, 530/339; 204/157.82; 502/232, 233; 562/561, 575

[56] References Cited

U.S. PATENT DOCUMENTS

| | | | |
|---|---|---|---|
| 4,280,992 | 7/1981 | Sugiura et al. | 436/527 |
| 4,927,952 | 5/1990 | Gueyne et al. | 556/419 |
| 4,985,405 | 1/1991 | Gueyne et al. | 514/8 |
| 5,229,096 | 7/1993 | Cohen | 423/338 |

FOREIGN PATENT DOCUMENTS

| | | |
|---|---|---|
| 8389 | 1/1988 | Japan . |
| 8390 | 1/1988 | Japan . |

OTHER PUBLICATIONS

*Journal of Biomedical Materials Research*, vol. 6, No. 5, "The Epitaxy of Poly–L–Alanine on L–Quartz and a Glass–Ceramic," Hartwig et al, pp. 413–474 (1972).

*Chem. Rev.*, vol. 90, No. 1, "The Sol–Gel Process," Hench et al, pp. 33–72 (1990).

*J. Am. Ceram. Soc.*, vol. 74, No. 7, "Bioceramics: From Concept to Clinic," Hench, pp. 1487–1510 (1991).

*Bioceramics*, vol. 5, "Reaction Kinetics of Bioactive Ceramics Part V: Molecular Orbital Modeling of Bioactive Glass Surface Reactions," West et al, pp. 75–86 (1992).

*Biocermaics*, vol. 6, "The Kinetics of Bioactive Ceramics Part VI: Silica–Water–Amino Acid Interactions," Hench et al, pp. 35–40 (1993).

*Journal of Non–Crystalline Solids*, vol. 152, "Interactions of water with trisiloxane rings. I. Experimental analysis," Wallace et al, pp. 101–108 (1993).

*Journal of Non–Crystalline Solids*, vol. 152, "Interactions of water with trisiloxane rings. II. Theoretical analysis," West et al, pp. 109–117 (1993).

*Journal of Biomedical Materials Research*, vol. 28, No. 5, "AM–1 molecular orbital calculations of silica–alanine–nitrogen interaction," West et al, pp. 625–633 (1994).

*Primary Examiner*—Jeffrey E. Russel
*Attorney, Agent, or Firm*—Kerkam, Stowell, Kondracki & Clarke; Dennis P. Clarke

[57] ABSTRACT

A method for synthesizing polypeptides from amino acids and/or peptides utilizing a novel reaction medium containing a hydrated silica entity containing silanol groups which function as an inorganic enzyme.

18 Claims, 15 Drawing Sheets

AM1 OPTIMIZED ALANINE MOLECULE
[$CH_3 - CH(NH_2) COOH$]

REPEAT UNIT OF CRYSTALLINE POLY-L-ALANINE = 8.55° A
AM1 HEAT OF FORMATION = -104.6 kcal/mol

AM1 OPTIMIZED CYCLOTRISILOXANE

AM1 HEAT OF FORMATION = -727.57 KCAL/MOL
(MODEL BB13)

TRANSITION STATE BETWEEN COOH (ala) CONDENSATION TO CYCLOTRISILOXANE AND $D_2$ RING OPENING INTO A CHAIN

AM1 HEAT OF FORMATION = -830.0 KCAL/MOL
MOPAC 6.1 CALCULATION
(MODEL M25)

TRANSITION STATE DURING NH$_2$ GROUP (ala) CONDENSATION TO CYCLOTRISILOXANE AND RING OPENING

AM1 HEAT OF FORMATION = -793.8 KCAL/MOL
MOPAC 6.1 CALCULATION
(MODEL M28)

STEP 6

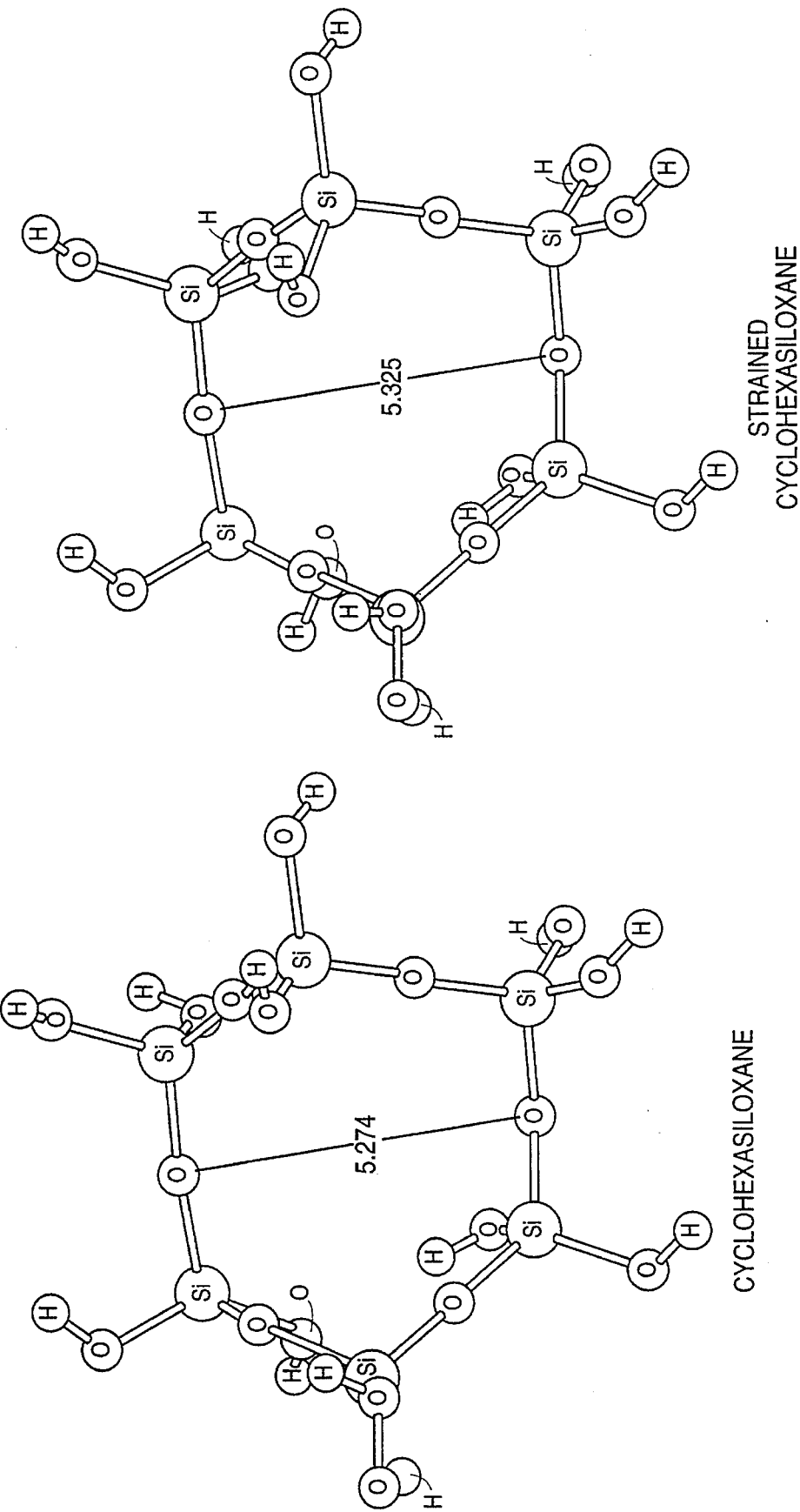

TWO EDGE SHARING CYCLOTETRASILOXANE
PLUS A WATER MOLECULE

TRANSITION STATE (SADDLE POINT)

SILICA MEDIATED SYNTHESIS OF PEPTIDES

BACKGROUND OF THE INVENTION

Research leading to the completion and reduction to practice of the invention was supported, in part, by Grant No. 49620-92-J-0351 issued by the U.S. Air Force Office of Scientific Research. The United States Government has certain rights in and to the claimed invention.

1. Field of the Invention

The present invention relates to novel methods for the synthesis of polypeptides.

2. Description of the Prior Art

Protein or polypeptide synthesis in nature requires the presence of enzymes which function as catalytic substrates, directing the reaction pathways for coupling amino acids with each other and with peptides via the so-called peptide linkage, —OC—NH—. The catalytic enzymes also enable the amino acid and/or peptides to overcome the energy barriers to the formation of the peptide linkages.

Numerous synthetic methods have been suggested heretofore for preparing polypeptides. It is an object of the present invention to provide a novel method for synthesizing polypeptides.

It is a further object of the invention to provide a novel reaction medium useful for the preparation of polypeptides.

SUMMARY OF THE INVENTION

These and other objects of the invention are realized by the present invention, one embodiment of which is a method for synthesizing a polypeptide comprising forming an aqueous reaction medium containing a first amino acid or peptide, a second amino acid or peptide and a hydrated silica entity containing silanol groups (HSE) in amounts and under conditions such that (1) at least one silanol group of the HSE undergoes a condensation reaction with a —COOH or —NH$_2$ group of one of the first amino acid or peptide to form a Si—O—CO— or Si—N—C— linkage, respectively, therewith and (2) thereafter, the second amino acid or peptide undergoes a condensation reaction with the HSE at the Si—O—CO— or Si—N—C— linkage via a —NH$_2$ or —COOH group, respectively, to form a peptide linkage, —OC—N—C—, in a polypeptide.

A further embodiment of the invention relates to a reaction medium for synthesizing polypeptides comprising an aqueous reaction medium containing a first amino acid or peptide, a second amino acid or peptide and a hydrated silica entity containing silanol groups.

An additional embodiment of the invention relates to a reaction medium in kit form suitable for admixing to synthesize polypeptides comprising, separately, (1) silica which, when admixed with water, is at least partly converted to a hydrated silica entity containing silanol groups, (2) a first amino acid or peptide and (3) a second amino acid or peptide.

DETAILED DESCRIPTION OF THE INVENTION

The present invention is predicated on the discovery that certain hydrated silica entities containing silanol groups (HSE) in the presence of amino acids and/or peptides function as "inorganic enzymes" in that they provide a catalytic-like pathway for overcoming the energy barrier to the formation of peptide linkages (—OC—NH—) between the amino acids and/or peptides to form polypeptides.

It has been discovered, for example, that an H$_2$O molecule adsorbs onto three-membered silica rings (cyclosiloxanes) with only a small activation barrier (+2.8 kcal/mol) hydrolyzing the siloxane bond, which opens the ring into a three-membered chain via a dissociative proton-transfer process involving the formation of a metastable transition state containing a pentavalent Si atom. It has been found that this penta-coordinate Si atom provides the low energy transition state that renders the hydrolysis-condensation reaction easily reversible.

Figure 1:
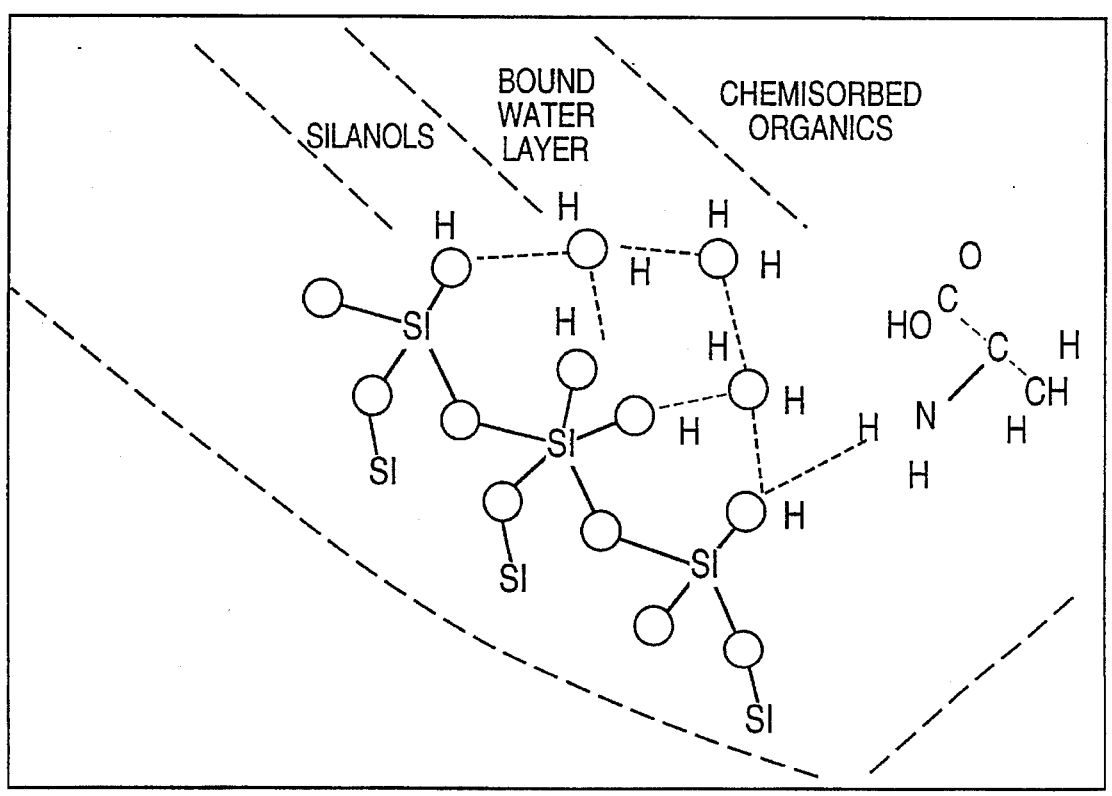
FIG. 1 is a schematic diagram of organic-inorganic interactions with porous hydrated silica.

Silica gel pore radii are 1.2 nm (12 Å) which are half-filled with tightly bound, highly structured pore water under fully hydrated conditions. The surface of the pores consist of a mixture of trisiloxane and tetrasiloxane rings with the relative proportion dependent on the extent of hydration of the gel and thermal history. Surface trisiloxane rings are strained in comparison to larger four-membered and five-membered rings so they are metastable and hydrolyze very quickly on contact with water molecules. Hydrolysis transforms the strained ring into a strain-free trisiloxane chain. However, the energy barrier for trisiloxane ring hydrolysis is so low (+2.8 kcal/mol) that a silica gel surface at 37° C. will consist of fluctuating rings and chains with formation of metastable penta-coordinate silicon atoms providing the low energy pathway between them. Any amino acid or peptide exposed to this environment will interact with the inorganic hydrated silica surface through a terminal —COOH group or through a terminal —NHH group (as depicted in FIG. 1).

Figure 2:
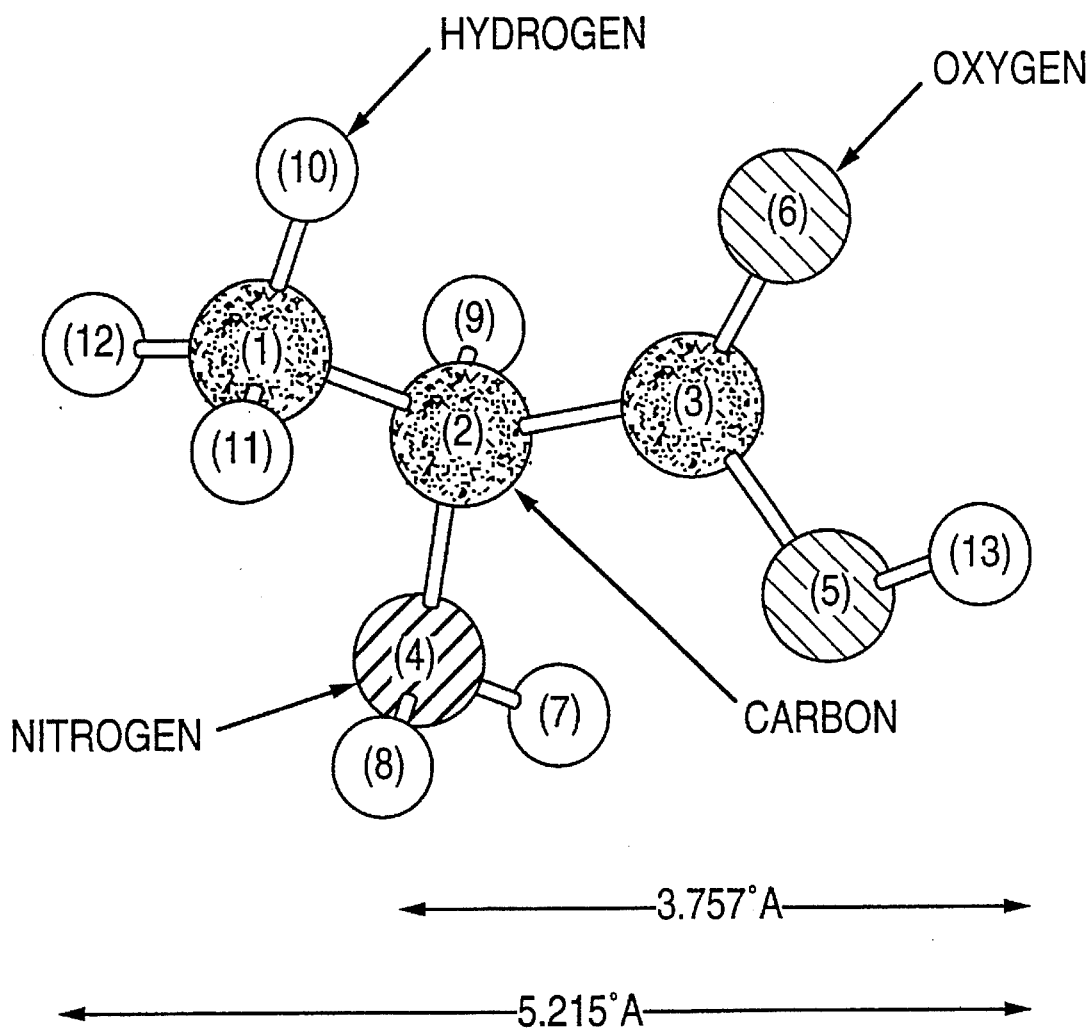
FIG. 2 is a diagram of a molecule of alanine.

The AM-1 (Austin Method) molecular orbital (MO) modeling method is employed to calculate the interactions of amino acids with silica clusters. The AM-1 method is a quantum mechanical self-consistent field method of calculation which is parameterized to yield good values for geometries and energies of interactions between atoms. FIG. 2 depicts the AM-1 optimized structure for the alanine molecule with the molecular dimensions indicated. Subsequent calculations compare the relative energy of interaction between the —COOH group of the alanine molecule and a hydrated silica cluster versus the energy of interaction of the —NHH group of alanine.

Figure 3:
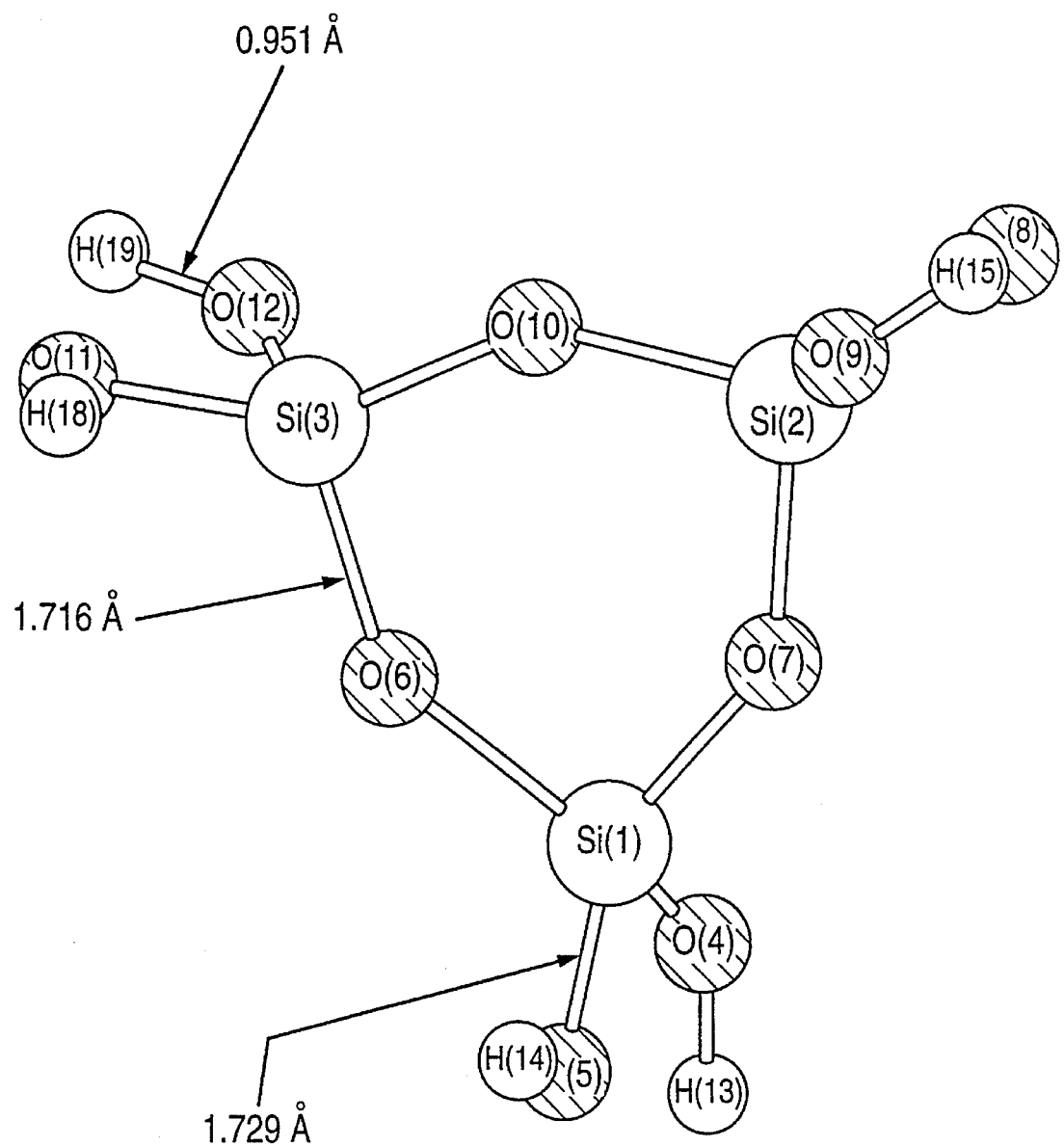
FIG. 3 is a diagram of a molecule of cyclotrisiloxane.

FIG. 3 shows the cyclotrisiloxane (Raman D$_2$ ring) as optimized in the AM-1 calculation. The heat of formation is −727.6 kcal/mol. There are three siloxane bonds; each silicon atom shares two. Each silicon also has two silanols.

Figure 4A:
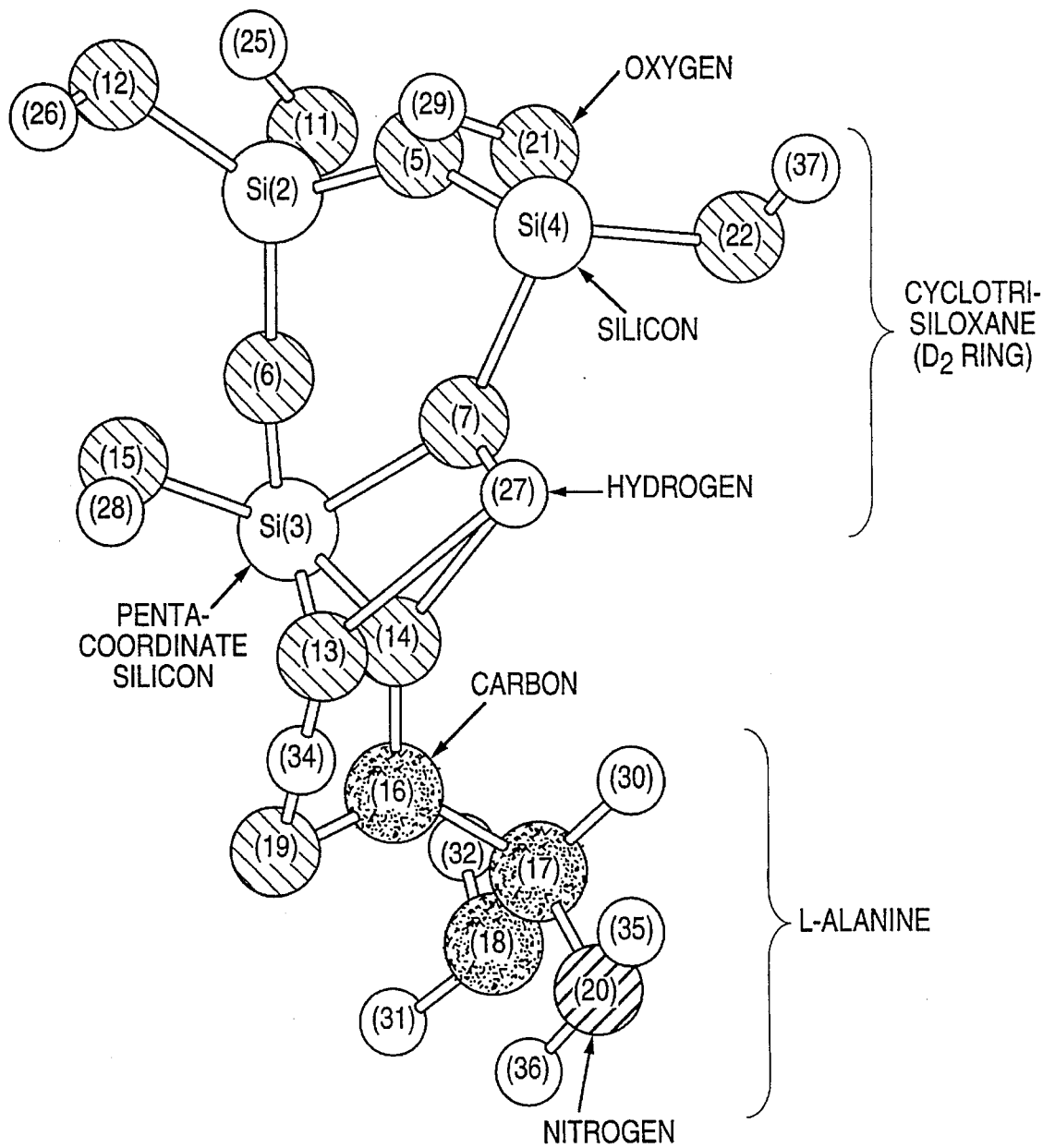
FIGS. 4a and 4b are diagrams of molecular reaction products of cyclotrisiloxane and alanine.
Figure 4B:
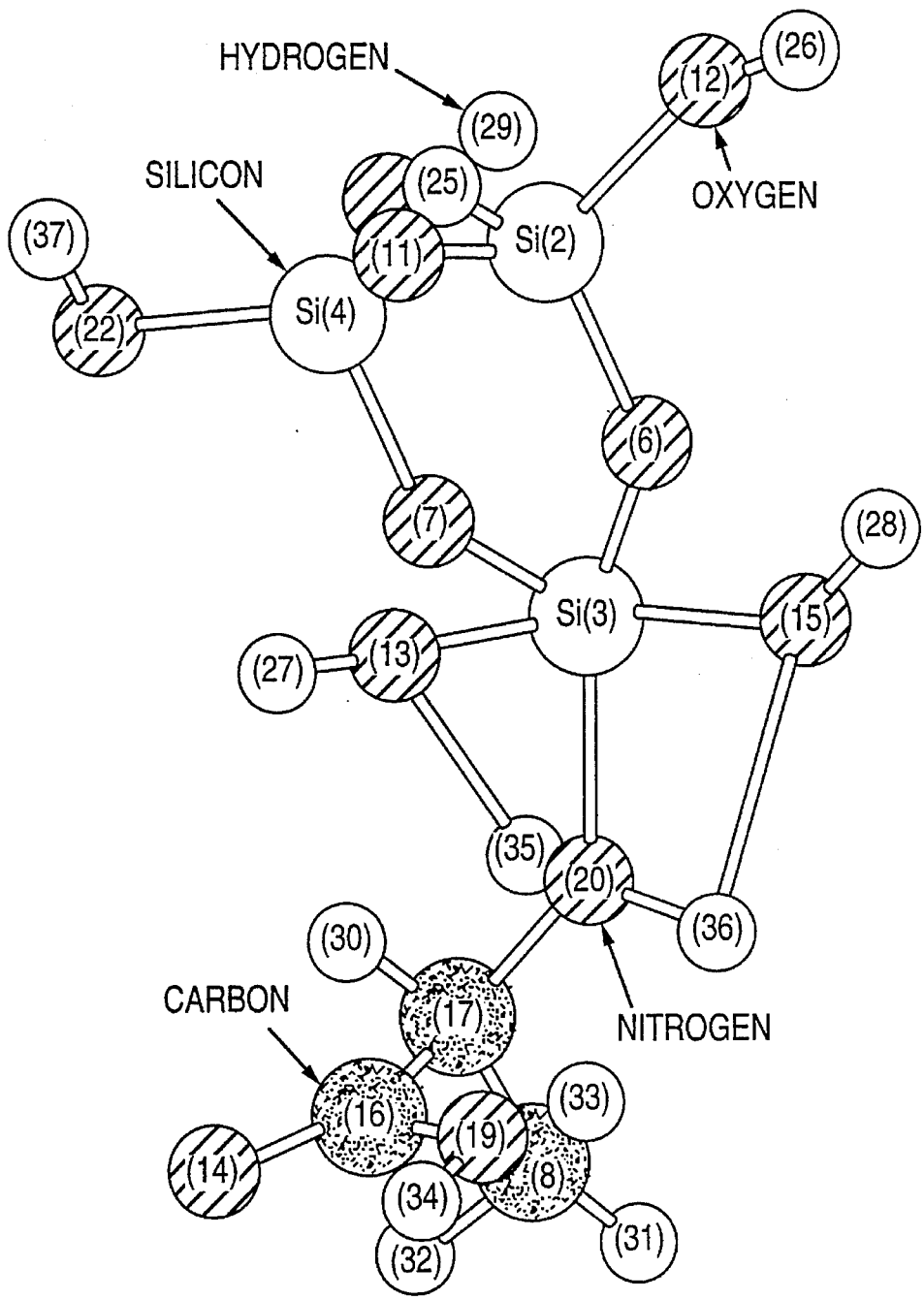
Figure 4C:
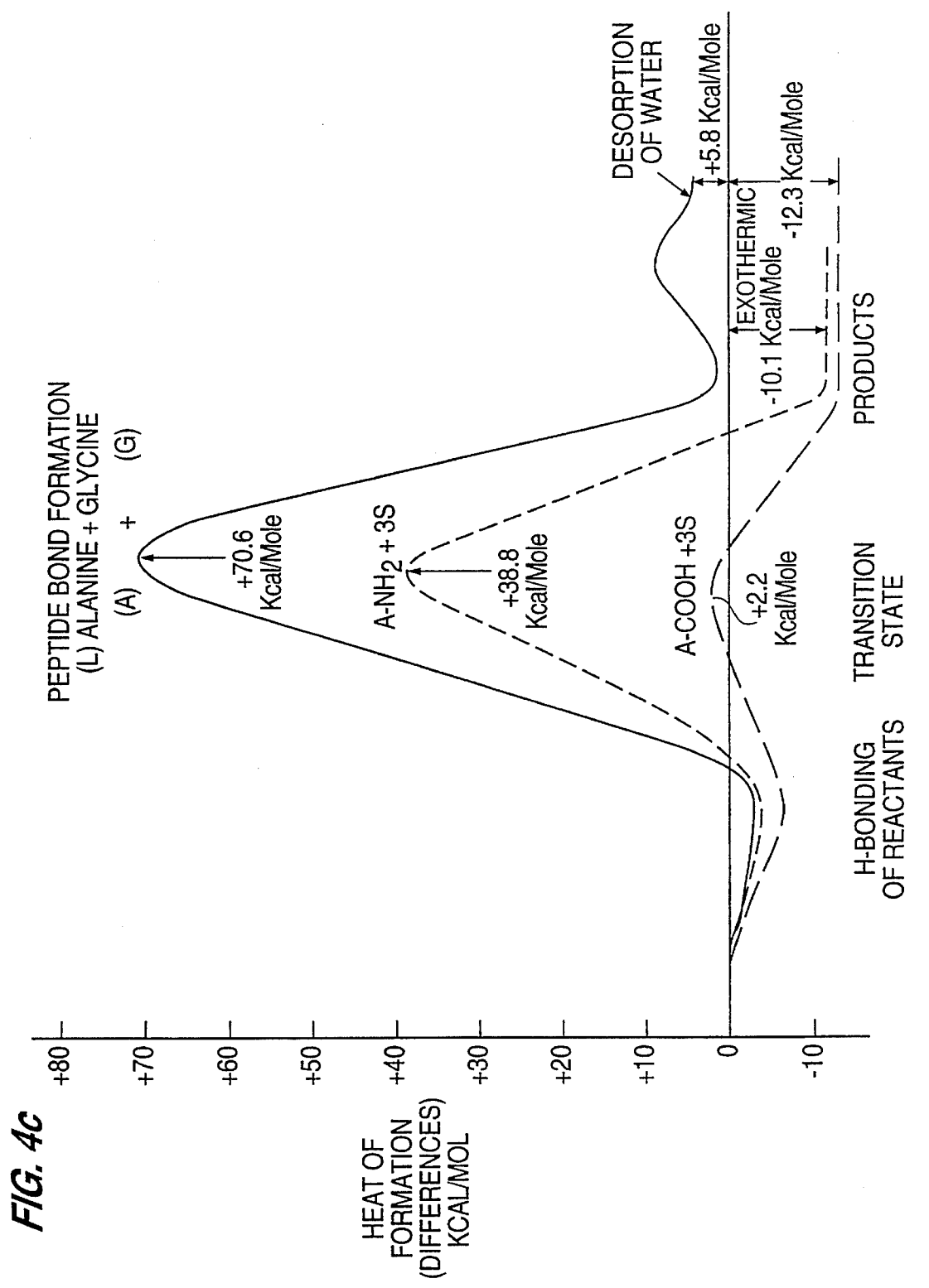
FIG. 4c is a diagram of the activation energies of various of the reactions occurring in the method of the invention.
Figure 5A:
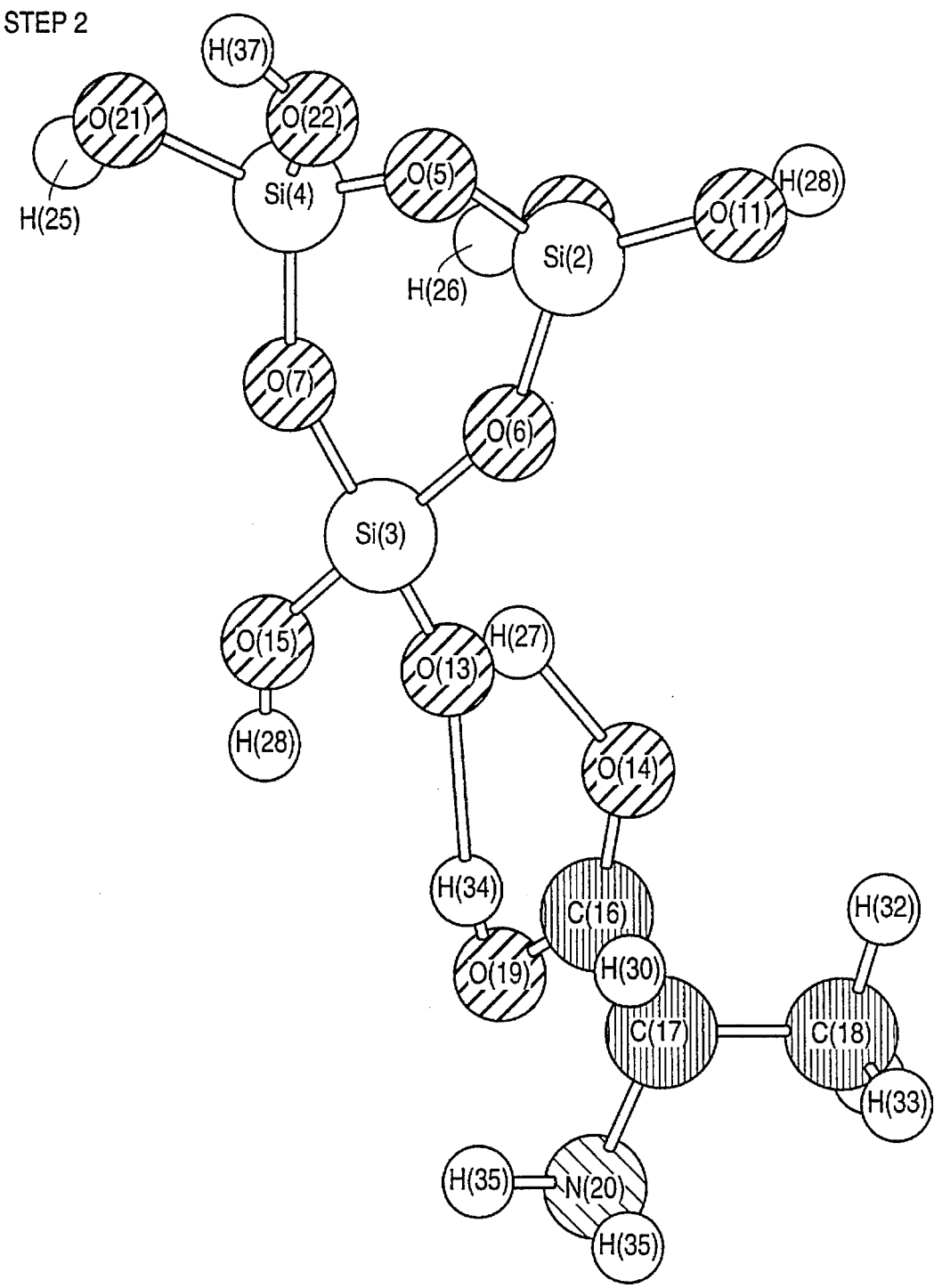
FIG. 5 is a partial reaction scheme of the method of the invention.
Figure 5B:
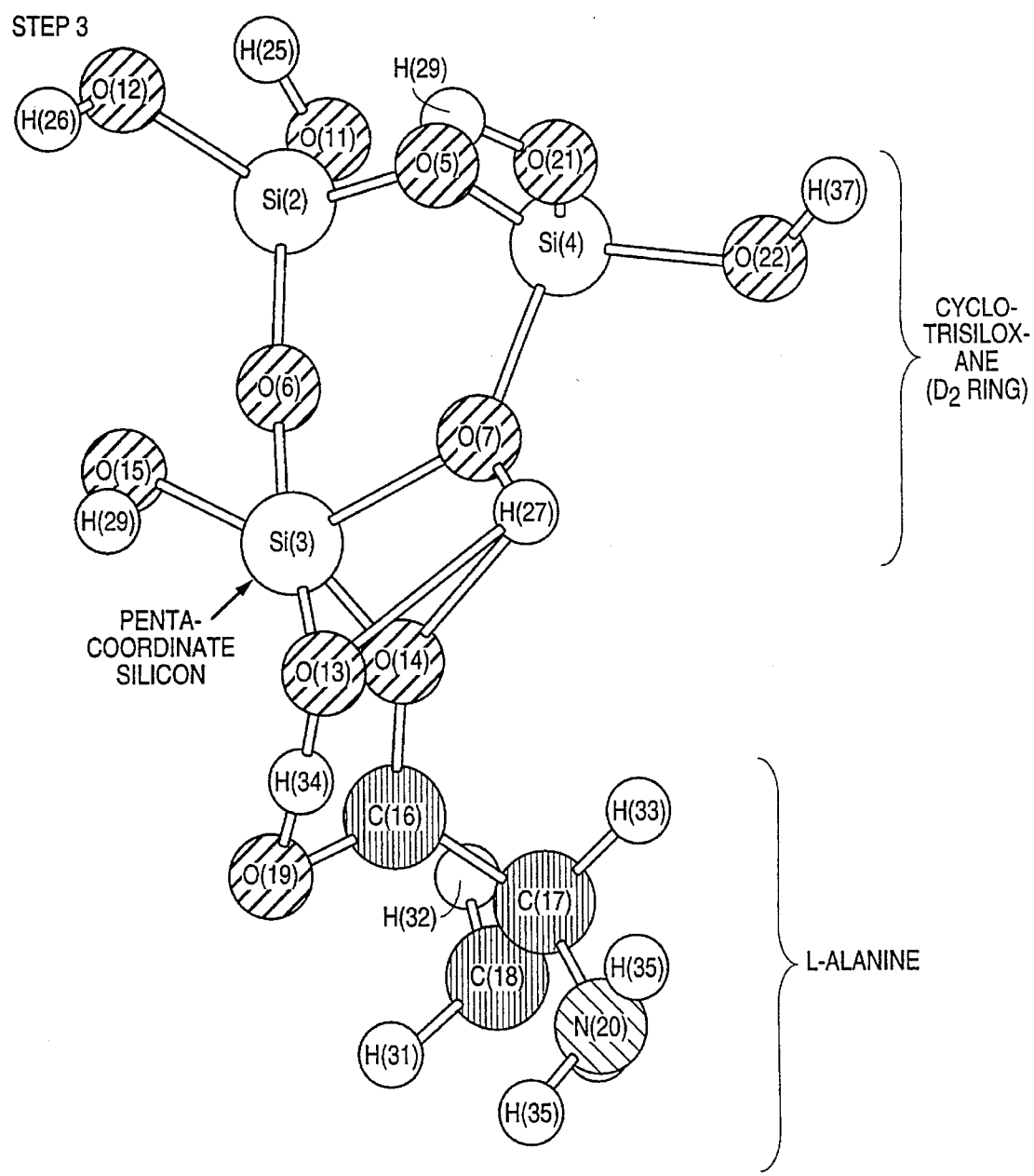
Figure 5C:
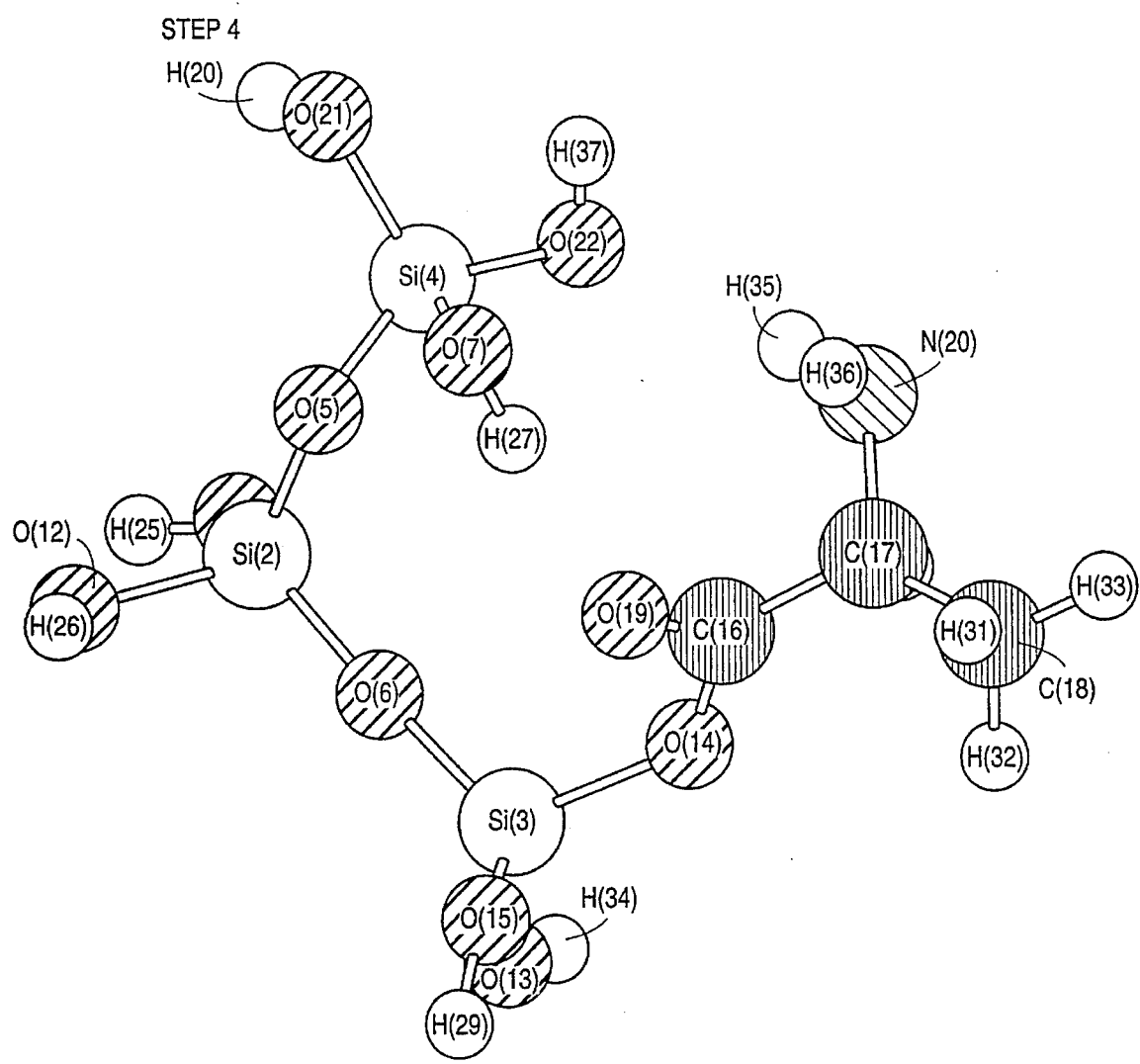
Figure 5D:
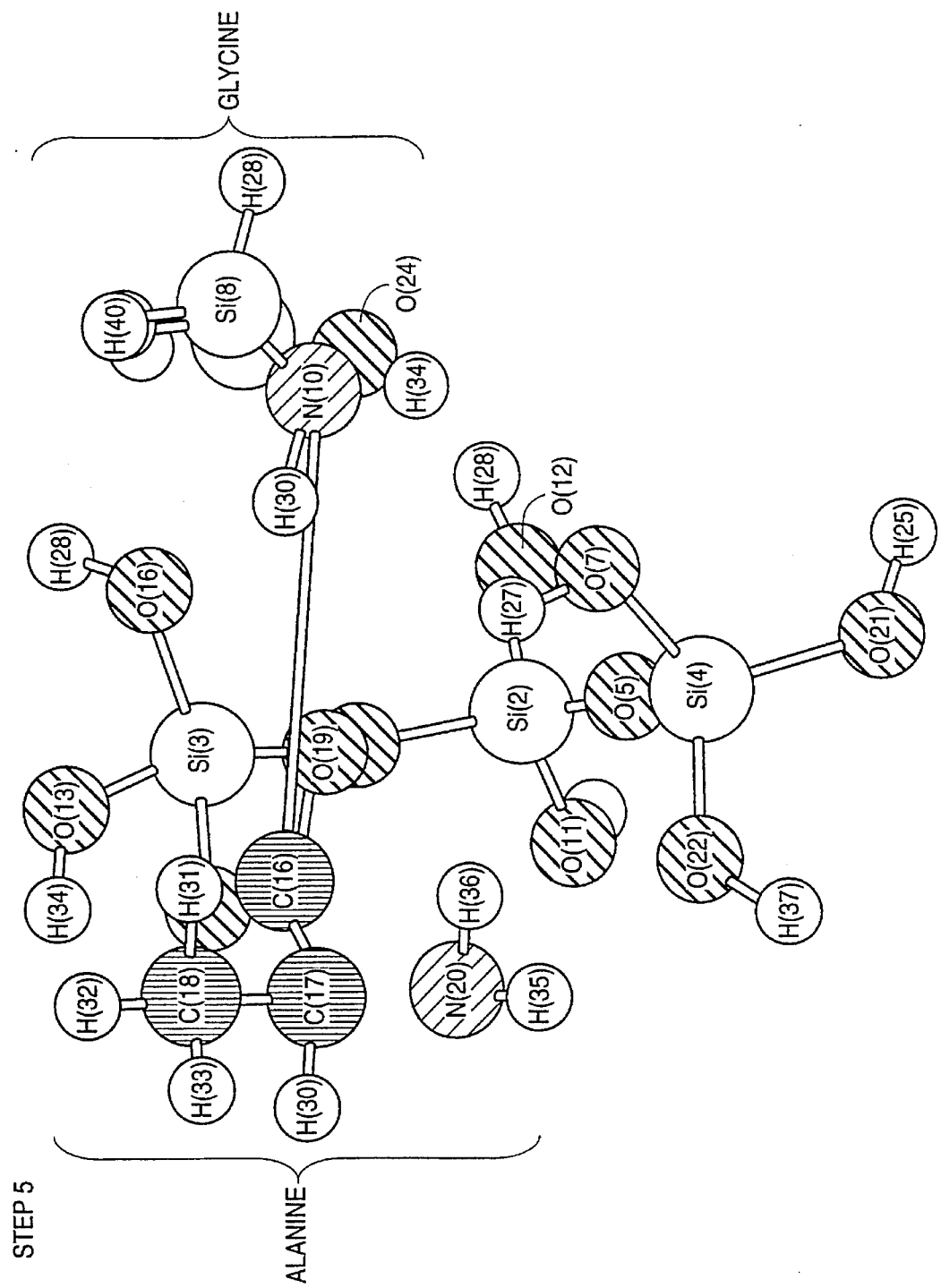
Figure 5E:
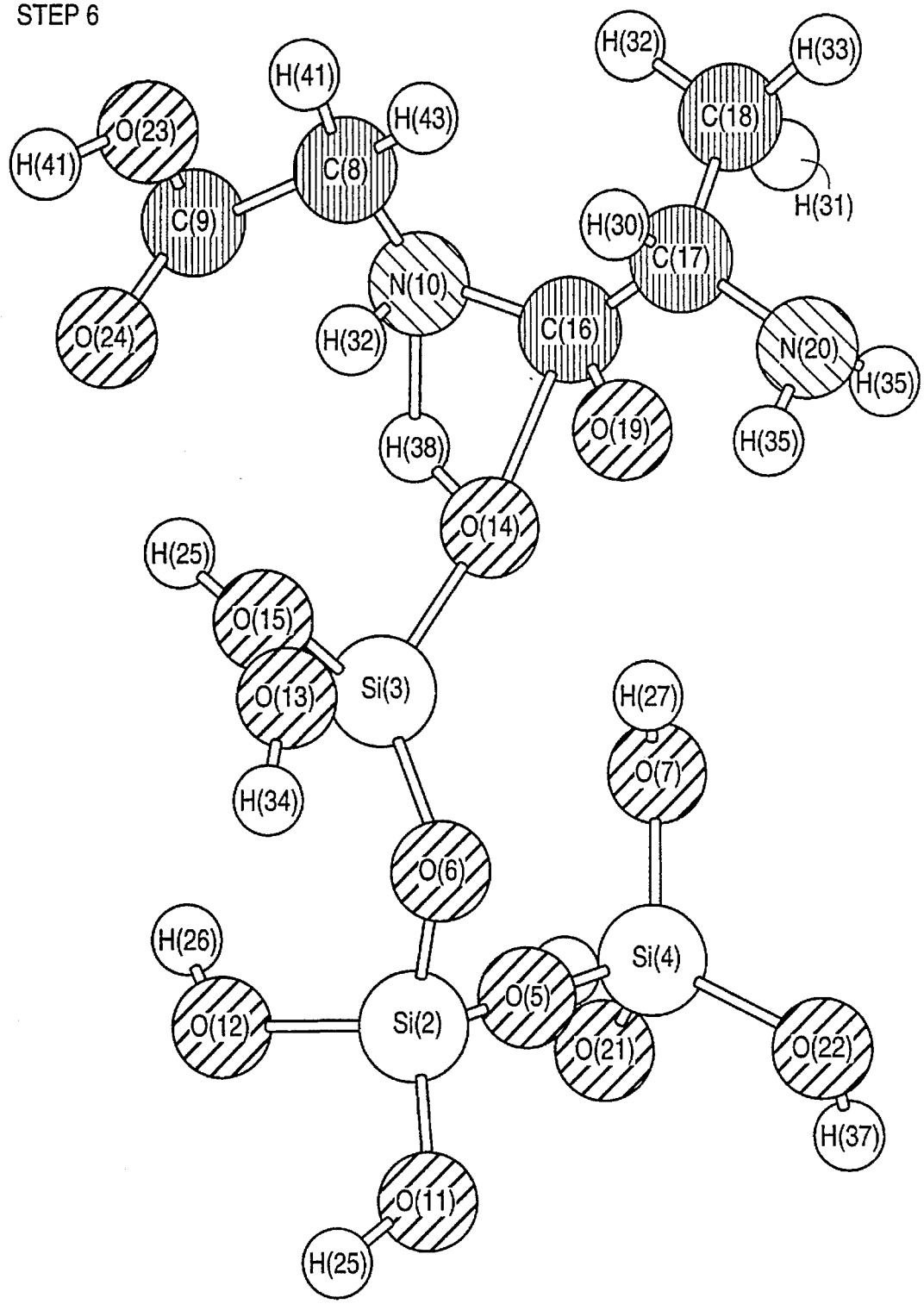
Figure 5F:
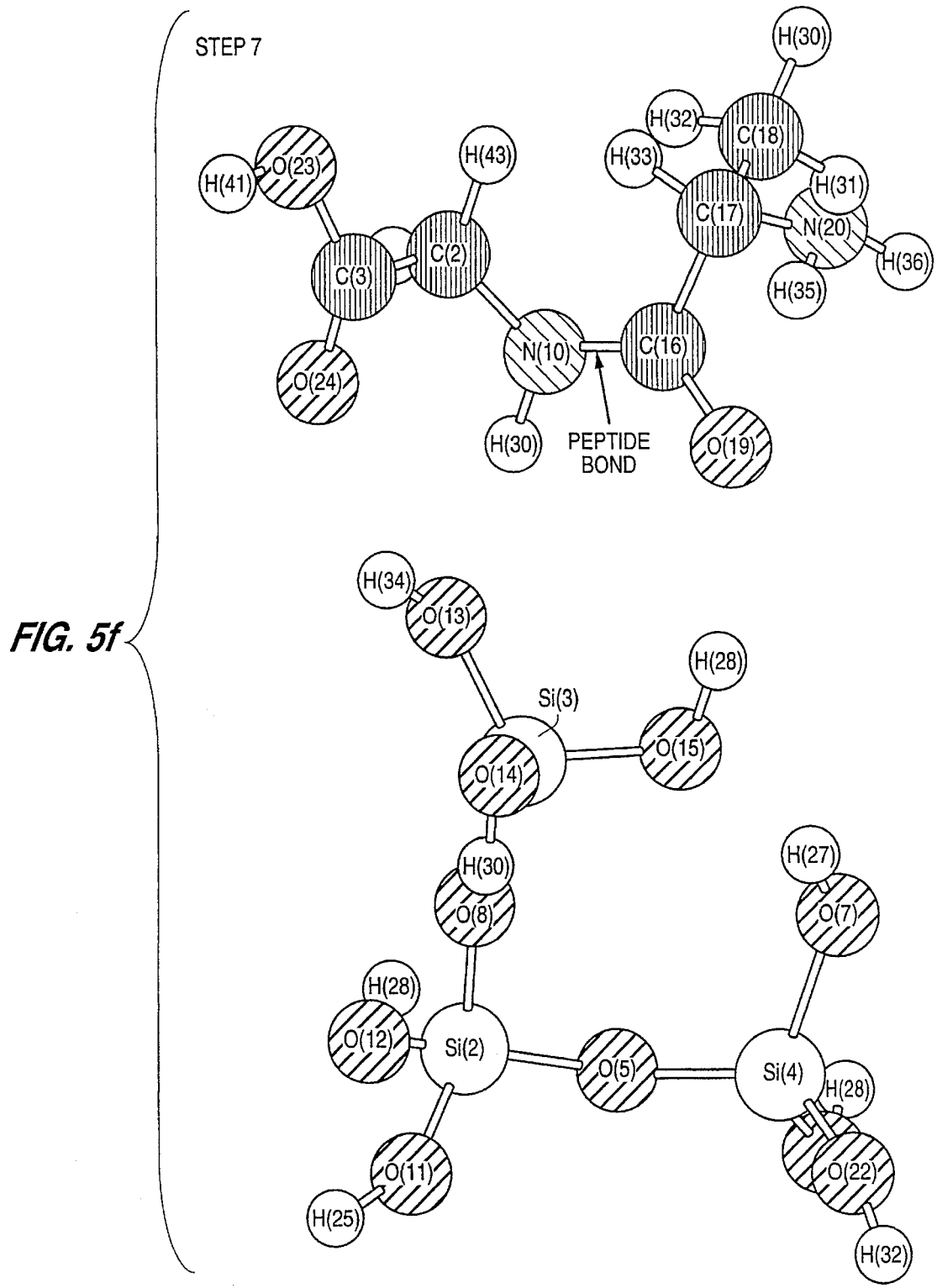

FIGS. 4a and 4b summarize the reaction pathway of alanine bonding to a cyclotrisiloxane cluster. The transition state associated with forming the alanine bond via the —COOH group is shown in FIG. 4a and the transition state for forming the bond via the —NHH group is depicted in FIG. 4b. The energetics of the reaction sequence to form the alternative types of bonds are compared in FIG. 4c. The activation energy required to form an alanine-glycine peptide bond without the catalytic aid of HSE, calculated using the same AM-1 method, is 70.6 kcal/mol and is shown for comparison.

These calculations show that the inorganic-organic bonding occurs in several steps. The first step is development of a hydrogen bond between the polar groups on the alanine with neighboring silanols on the silica cluster. The next step in the reaction is the formation of a penta-coordinate Si transition state which ultimately results in a ring-opening as a chemical bond is formed between the inorganic cluster and the organic molecule. This is a condensation reaction similar to formation of a dipeptide bond between two amino acids. There is a very large difference in the energy barrier, however, depending on which group of the alanine molecule is involved (see FIG. 4c).

The product of the condensation reaction is a silica-alanine cluster with a Si—O—C bond. This final alanine—COOH reaction has a barrier of +2.2 kcal/mol. In the case of the alanine-NHH reaction, the barrier is +38.8 kcal/mol. The bond energy of the inorganic-organic complex is between —10.1 and —12.3 kcal/mol.

The MO calculation results show that there are low energy reaction pathways for organic-inorganic reactions between alanine molecules and hydrated silica clusters. The energy barrier is very much lower than the barrier that exists for formation of a dipeptide bond between alanine and glycine, calculated using the same AM-1 method (see FIG. 4c). The large energy barrier for peptide bond formation is circumvented in biological systems by enzymes, which are specific for each type of dipeptide formed. However, the calculations presented herein show that inorganic surfaces can provide a catalytic-like function in the binding of organic molecules similar to that of enzymes. Similar results were obtained for the interaction of alanine with tetrasiloxane rings. However, the four-membered silica rings have a substantially higher activation barrier for the alanine —COOH interaction, i.e., +24 kcal/mol. The barrier to the —NHH interaction is about the same, i.e., +49.4 kcal/mol.

FIG. 5 depicts a partial reaction sequence of molecular models for alanine-glycine dipeptide formation using the method of the invention. Again, the low energy barriers to form silica-amino acid bonds are due to the formation of penta-coordinate Si in a metastable transition state (FIG. 5, Step 3). The penta-coordinate state occurs when the —COOH group of alanine interacts with trisiloxane or tetrasiloxane rings. The —COOH interaction yields the lowest energy barriers and forms a —Si—O—C bond. The silica-amino acid chains formed from the trisiloxane rings are energetically downhill and stable at −10 to −12 kcal/mol. This allows for the bonding of any peptide or protein to the silica surface.

Figure 6:
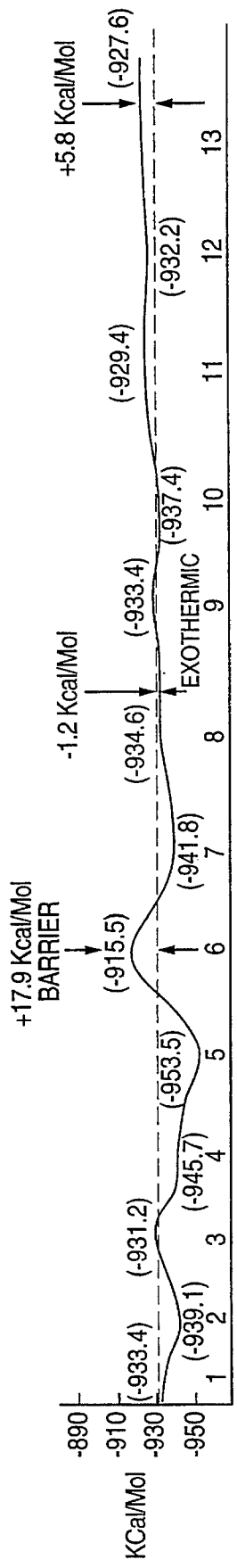
FIG. 6 is a diagram of the reaction energy pathways for the method of the invention.

The metastable penta-coordinate Si—OH complex acts like an inorganic enzyme in providing an energetically favorable reaction pathway for polypeptide synthesis. The reversible opening and closing of the hydrated silica rings provides the low energy pathway and the penta-coordinate Si transition state provides the enzymatic function. The steps for inorganic peptide bond formation are shown in the thirteen steps listed in Table 1. Steps 1–4 start with a trisiloxane ring plus alanine and glycine and go to a trisiloxane-alanine chain plus glycine. Steps 4–7 start with the chain-alanine plus glycine and end up with a trisiloxane chain plus alanine-glycine dipeptide. Finally, in Steps 8–13, the trisiloxane chain plus dipeptide yields a trisiloxane ring plus dipeptide. The reaction pathway for this inorganic route to biosynthesis is much lower in energy than direct alanine-glycine condensation. The complete reaction pathways are shown in FIG. 6.

TABLE 1

| Reaction Steps | Interactions* (where and = no interaction) | $H_f$ | Kcal/mol |
| --- | --- | --- | --- |
| 1 | D2 and A and G | −933.4 | 0.0 |
| 2 | A + H-bonded D2 and G | −939.1 | −5.7 |
| 3 | A + D2 to S saddle and G | −931.2 | +2.2 |
| 4 | AS Chain and G | −945.7 | −12.3 |
| 5 | AS Chain + H-bonded G | −953.5 | −20.1 |
| 6 | A + G + S Saddle | −915.5 | +17.9 |
| 7 | AG Dipeptide + bonded S | −941.8 | −8.4 |
| 8 | AG Dipeptide and S | −934.6 | −1.2 |
| 9 | S to D2 Saddle and AG | −933.4 | 0.0 |
| 10 | Penta-coordinate D2 and AG | −937.4 | −4.0 |
| 11 | Penta-coordinate Saddle and AG | −929.4 | +4.0 |
| 12 | D2 + H-bonded $H_2O$ and AG | −932.2 | +1.2 |
| 13 | D2 and $H_2O$ and AG Dipeptide | −927.6 | +5.8 |

D2 = cyclotrisiloxane; A = alanine; G = glycine; S = trisiloxane chain; AG = dipeptide The term "saddle" in the present context is the point on the energy surface between two stable states wherein the second derivative of the energy is negative in only one mode of the force matrix.

If an internal or cartesian coordinate can be identified with the reaction coordinate, then by monotonically increasing or decreasing the coordinate, the energy profile of the reaction path can be mapped. The transition state is, of course, the highest point of the lowest energy path.

The reaction path is very complicated in the silica-alanine-glycine reaction, for example. In that case, the transition state can be approached from two directions simultaneously. The method, known as the "saddle" technique, would then be used for locating the transition state.

Once a rough approximation to the transition state has been obtained, gradient minimization and UHF (unrestricted Hartre-Fock theory) techniques can be used for refining the system. The most commonly used techniques are the Bartels and McIver-Komornicki methods.

Finally, the transition state must be characterized by evaluating all the force constants. With rare exceptions, a transition state must have exactly one negative force constant. The exceptions arise from group theory requirements.

The following steps correspond to calculational models:
1=BB13, M2, P2
2=M23, P
3=M25, P2
4=M24, P2
5=M32
6=M33
7=M30
8=P3, M3
9=TrlB-3.2, P3
10=R3OHH, P3
11=R3W-2.9, P3
12=R3H₂O, P3
13=BB13, H₂O, P3.

The heat of formation of the final dipeptide bond is calculated to be +5.8 kcal/mol. This is equivalent to literature values for peptide bonds. The overall reaction barrier for this sequence of peptide synthesis is +17.9 kcal/mol. This is greater than a barrier for peptide formation via enzyme action, but significantly less than the +70.6 kcal/mol barrier to direct peptide formation.

Figure 7D:
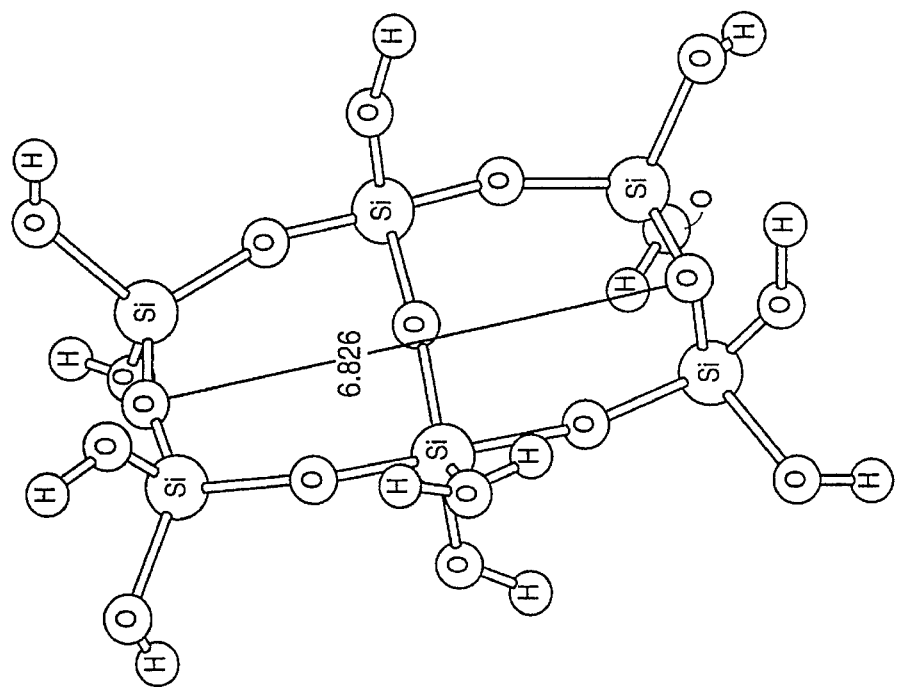
FIG. 7 is a diagram showing the transition states of cyclohexasiloxane under strain.
Figure 7C:
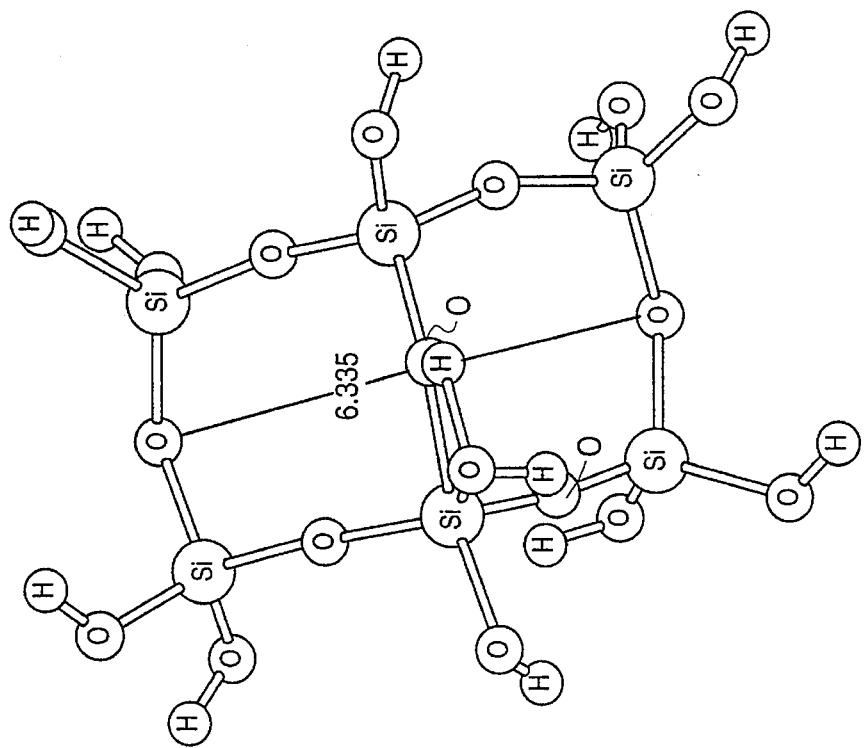

Any HSE capable of catalyzing the formation of the peptide linkage between amino acids and/or peptides via the formation of reactive metastable penta-coordinate Si-OH complex intermediate may be employed in the practice of the invention. Suitable such HSE's include any which provide a favorable energy of formation pathway for the formation of the peptide linkage and include cyclopolysiloxanes such as cyclodisiloxane, cyclotrisiloxane, cyclotetrasiloxane and higher cyclopolysiloxanes which contract under strain or chemical reaction to form lower ordered (2- or 3-membered) rings; e.g., cyclopentasiloxane, cyclohexasiloxane, cycloseptasiloxane, cyclooctasiloxane and the like. Thus, contraction of a 6-fold (cyclohexasiloxane) ring is shown in FIG. 7 to be a step-wise sequence in which the 6-fold ring will contract into a pair of edge sharing 4-fold rings if strain is applied. It is interesting to note that in this study, energy is released (i.e., the sequence is exothermic) as the process goes from 7A→7D. The saddle point (transition state) represents a +8 to +9 kcal/mol barrier which is very much like the release of energy when a 3-fold ring goes into a 3-fold chain under strain in the presence of water as described in the sequence in steps 1–4 of Table 1.

As described above, the HSE can react in alternative ways with the amino acid, i.e., through the —COOH group or the —NH$_2$ group.

In the case of reaction with the —COOH group, the silanol group of the HSE undergoes the condensation reaction with a —COOH group of the first amino acid or peptide to form a Si—O—CO— linkage therewith and thereafter, the second amino acid or peptide undergoes the condensation reaction with the HSE at the Si—O—CO— linkage via a —NH$_2$ group to form the peptide linkage in the peptide.

More particularly, the condensation reaction of the silanol group of the HSE with a —COOH group of the first amino acid or peptide comprises:

(a) a first reaction of the —COOH group with the silanol and surrounding silanol groups of the HSE to form a hydrogen bonded intermediate;

(b) a second reaction wherein the —COOH group reacts with the silanol group in the hydrogen bonded intermediate to form the Si—O—CO— linkage in a metastable intermediate wherein the silicon atom in the Si—O—CO— linkage is in a penta-coordinate transition state; and (c) a final reaction wherein the metastable intermediate loses a molecule of water resulting in a conversion of the silicon atom from a penta-coordinate transition state to a stable tetra-coordinate state.

Where the HSE is a cyclopolysiloxane and the hydrogen bonded intermediate and metastable intermediate are cyclopolysiloxane derivatives, the third reaction (c) results in a ring opening of the cyclopolysiloxane to form a linear polysiloxane containing the Si—O—CO— linkage.

In those cases involving reaction of the —NH$_2$ group of the amino acid or peptide, the silanol group of the HSE undergoes the condensation reaction with a —NH$_2$ group of the first amino acid or peptide to form a Si—N—C— linkage therewith and (2) thereafter, the second amino acid or peptide undergoes the condensation reaction with the HSE at the Si—N—C— linkage via a —COOH group to form the peptide linkage in the peptide.

More particularly, the condensation reaction of the silanol group of the HSE with a —NH$_2$ group of the first amino acid or peptide comprises:

(a) a first reaction of the —NH$_2$ group with the silanol and surrounding silanol groups of the HSE to form a hydrogen bonded intermediate;

(b) a second reaction wherein the —NH$_2$ group reacts with the silanol group in the hydrogen bonded intermediate to form the Si—N—C— linkage in a metastable intermediate wherein the silicon atom in the Si—N—C— linkage is in a penta-coordinate transition state; and (c) a final reaction wherein the metastable intermediate loses a molecule of water resulting in a conversion of the silicon atom from a penta-coordinate transition state to a stable tetra-coordinate state.

Where the HSE is a cyclopolysiloxane and the hydrogen bonded intermediate and metastable intermediate are cyclopolysiloxane derivatives, the third reaction (c) results in a ring opening of the cyclopolysiloxane to form a linear polysiloxane containing the Si—N—C— linkage.

Suitable amino acids for reaction to form polypeptides according to the method of the invention include those having the formula:

R—CH(NHA)—COOH wherein R is H, alkyl, aryl, aralkyl; the alkyl or aralkyl groups optionally containing thioether or ether linkages or heterocyclic groups wherein the heteroring comprises carbon and nitrogen atoms; each of the groups optionally being substituted by —OH or —NH$_2$ groups and A is H or together with —CH(NH)— forms a heterocyclic group linked to —COOH via the —CH group and wherein the heteroring comprises carbon and nitrogen atoms. Suitable amino acids are listed in Table 2.

The amino acids of Table 2 mostly are of the generalized form each with a —COOH and a —NH$_2$ group. The positions of each of these groups (or structure) will determine the absolute barriers to the formation of the Si—O—C linkages or the Si—N linkages. Only one does not have an —NH$_2$; this is proline. Others have types 3, 4, 5 or 6 sites that would be active with respect to silica.

TABLE 2

AMINO ACIDS

| Amino Acid | Abbreviation | Formula + Potential Bond Types | # of Potential Bond Types | | | | | |
|---|---|---|---|---|---|---|---|---|
| | | | 1 | 2 | 3 | 4 | 5 | 6 |
| Alanine | ala | CH$_3$—CH—(COOH)-1 / (NH$_2$)-2 | 1 | 1 | | | | |
| Arginine | arg | 2-(H$_2$N)—C—NH—CH$_2$—CH$_2$—CH$_2$—CH—(COOH)-1 / (NH)-3 / (NH$_2$)-2 | 1 | 2 | 1 | | | |
| Asparagine | asn | 2-(H$_2$N)—C—CH$_2$—CH—(COOH)-1 / 4-(O) / (NH$_2$)-2 | 1 | 2 | | 1 | | |
| Aspartic Acid | asp | 1-(HOOC)—CH$_2$—CH—(COOH)-1 / (NH$_2$)-2 | 2 | 1 | | | | |
| Cysteine | cys | 5-(HS)—CH$_2$—CH—(COOH)-1 / (NH$_2$)-2 | 1 | 1 | | | 1 | |
| Glutamic Acid | glu | 1-(HOOC)—CH$_2$—CH$_2$—CH—(COOH)-1 / (NH$_2$)-2 | 2 | 1 | | | | |
| Glutamine | gln | 2-(H$_2$N)—C—CH$_2$—CH$_2$—CH—(COOH)-1 / O-4 / (NH$_2$)-2 | 1 | 2 | | 1 | | |
| Glycine | gly | H—CH—(COOH)-1 / (NH$_2$)-2 | 1 | 1 | | | | |
| Histidine | his | HC=C—CH$_2$—CH—(COOH)-1 / N, NH / (CH)-6 / (NH$_2$)-2 | 1 | 1 | | | | 1 |
| Isoleucine | ile | CH$_3$—CH$_2$—CH—CH—(COOH)-1 / CH$_3$ / (NH$_2$)-2 | 1 | 1 | | | | |

TABLE 2-continued
AMINO ACIDS
| Amino Acid | Abbreviation | Formula + Potential Bond Types | # of Potential Bond Types | | | | | |
|---|---|---|---|---|---|---|---|---|
| | | | 1 | 2 | 3 | 4 | 5 | 6 |
| Leucine | leu | 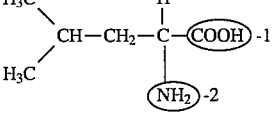 | 1 | 1 | | | | |
| Lysine | lys | 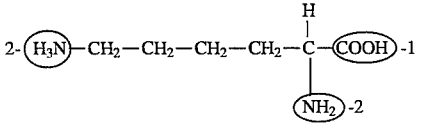 | 1 | 2 | | | | |
| Methionine | met | 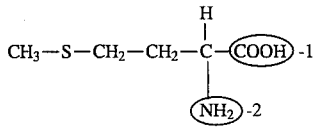 | 1 | 1 | | | | |
| Phenylalanine | phe | 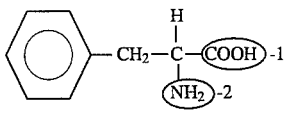 | 1 | 1 | | | | |
| Proline | pro | 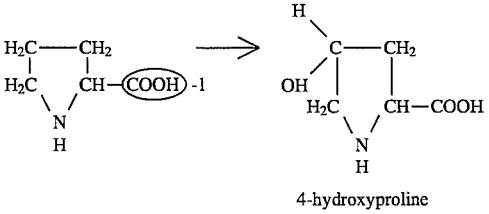<br>4-hydroxyproline | 1 | | | | | |
| Serine | ser | 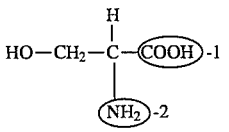 | 1 | 1 | | | | |
| Threonine | thr | 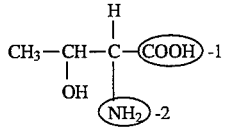 | 1 | 1 | | | | |
| Tryptophan | trp | 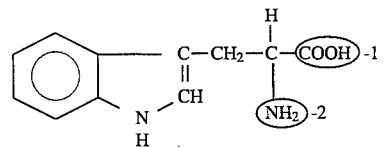 | 1 | 1 | | | | |
| Tyrosine | tyr | 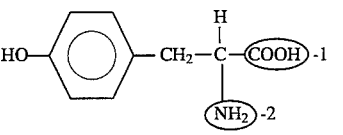 | 1 | 1 | | | | |

TABLE 2-continued

AMINO ACIDS

| Amino Acid | Abbreviation | Formula + Potential Bond Types | # of Potential Bond Types | | | | | |
|---|---|---|---|---|---|---|---|---|
| | | | 1 | 2 | 3 | 4 | 5 | 6 |
| Valine | val | H₃C\C—(COOH)-1 / H₃C (NH₂)-2 | 1 | 1 | | | | |

The method of the invention may be employed to synthesize virtually any polypeptide which could be prepared from any of the amino acids or lower order peptides described above according to any of the methods heretofore described in the prior art. Exemplary of polypeptides which may be prepared according to the method of the invention include those which may be produced by the sequential reaction of any of the amino acids listed in Table 2.

The polypeptide products may be recovered from the reaction medium by, for example, subjecting the reaction mixture to high speed centrifugation to separate the components of the mixture according to their differing molecular weights. Molecular sieves, reverse osmosis and chromatographic techniques could also be employed to isolate the reaction products.

Reactive groups on the amino acid or peptide reactants could, of course, be rendered inactive by masking with a conventional protective group to synthesize very specific sequences of amino acids to the exclusion of others which would be formed if the reactive sites were not protected. Those skilled in the art will be aware of conventional and well known techniques for modifying the method of the invention by employing protective groups where necessary.

Where the components of the reaction medium are separately packaged in kit form for later admixture, it will be understood by those skilled in the art that each of the silica, first amino acid or peptide or second amino acid or peptide may be dissolved or suspended in at least two separate aqueous media adapted for admixture with each other to form the reaction medium of the invention.

The invention is illustrated by the following non-limiting examples.

EXAMPLE 1

Porous Type VI sol-gel silica was prepared from tetramethoxysilane (TMOS) using HF and $H_2NO_3$ as catalysts. The gels were cast, aged, dried and stabilized to 600° C. The $N_2$ absorption analysis from the Quantachrome 6 showed these samples had a pore radius (PR) of 69.3 Å, pore volume (PV) of 0.05 cc/gm, and a surface area (SA) of 16.7 sq. m/g.

The gels were then ground into micron size powder. These powders were immediately weighed and poured into flasks containing deionized water (DIW) and the amino acid.

The amino acids, glycine and alanine were dissolved in deionized water at 1/10 their solubility limit, i.e., 2.52 gm glycine per 100 ml DIW and 1.06 gm alanine per 100 ml DIW (see Table 3).

TABLE 3

| Sample ID | Description |
|---|---|
| G + S | 2.52 gm glycine in 100 ml DIW + 3 gm sol-gel silica |
| A + S | 1.06 gm alanine in 100 ml DIW + 3 gm sol-gel silica |
| A + G + S | 2.52 gm glycine, 1.06 gm alanine in 100 ml DIW + 3 gm sol-gel silica |
| S | 3 gm sol-gel silica in DIW |
| A | Alanine Standard 1.07 gm in 200 ml DIW |

After the silica powders were added to the mixtures, the flasks were placed on an orbital mixing table set at 150 rpm and 37° C.

Samples were taken from the supernatant after 30 minutes of settling at weeks 2, 9 and 13.

HPLC Experimental Results

The High Power Liquid Chromatography (HPLC) results for the 2, 9, 13 and 14 week (A+S) samples are shown in Table 4. The area percent for the dipeptide peak (#2) grew from 0.169% to 0.285% over this period As can be seen, dipeptides are present in the standard; therefore, growth in the second peak is delayed. The growth ratio of peak #2 to peak #3 shows these changes very clearly.

Note also the alanine peak (#1) shows a small but consistent decrease in area from 98.671% to 98.664% to 98.564% after 13 weeks. This indicates consumption of alanine during the peptide synthesis.

TABLE 4

| | (A + S) | | | |
|---|---|---|---|---|
| Weeks | #1% Area | #2% Area | #3% Area | Growth Ratio 2:3 |
| Alanine Standard | 98.082 | 0.4159 | 1.503 | 0.28 |
| 2 | 98.671 | 0.169 | 1.047 | 0.16 |
| 9 | 98.664 | 0.243 | 1.028 | 0.24 |
| 13 | 98.564 | 0.285 | 1.151 | 0.25 |
| 14 | 98.523 | 0.303 | 1.173 | 0.26 |
| 14 | 98.668 | 0.269 | 1.062 | 0.25 |

The results in Table 5 show that additional sol-gel silica causes an increase in the growth of the dipeptide (#2) peak. At 11 weeks into the study, the (A+S) sample was split. Half continued in the normal manner, while the other half [designated ((A=S)+S)] had an additional 10 grams of sol-gel silica powder added. This positive result verifies that a specific three-membered ring structure ($D_2$) is consumed during the synthesis. Adding fresh porous silica resulted in a large increase in the area percent of peak #2.

TABLE 5

| Weeks | ((A + S) + S) | | | Growth Ratio 2:3 |
|---|---|---|---|---|
| | #1% Area | #2% Area | #3% Area | |
| 11 + 2 | 98.597 | 0.343 | 1.061 | 0.32 |
| 11 + 3 | 98.555 | 0.378 | 1.067 | 0.35 |

Ultraviolet responses of the silica-alanine and silica-glycine complexes in experimental tests indicate that UV irradiation of the reaction enhances the formation of the Si—O—C— and Si—N— linkages thereby increasing the yields of the final product and facilitating the reaction.

We claim:

1. A method of synthesizing a polypeptide comprising forming an aqueous reaction medium containing a first amino acid or peptide, a second amino acid or peptide and a hydrated silica entity containing silanol groups (HSE) in amounts and under conditions such that (1) at least one silanol group of said HSE undergoes a condensation reaction with a —COOH or —NH$_2$ group of one of said first amino acid or peptide to form a Si—O—CO— or Si—N—C— linkage, respectively, therewith and (2) thereafter, said second amino acid or peptide undergoes a condensation reaction with said HSE at said Si—O—CO— or Si—N—C— linkage via a —NH$_2$ or —COOH group, respectively, to form a peptide linkage, —OC—N—C—, in said polypeptide.

2. The method of claim 1 wherein said HSE is a cyclopolysiloxane.

3. The method of claim 2 wherein said HSE is a cyclopolysiloxane selected from the group consisting of cyclodisiloxane, cyclotrisiloxane, cyclotetrasiloxane, cyclopentasiloxane, cyclohexasiloxane, cycloseptasiloxane and cyclooctasiloxane.

4. The method of claim 1 wherein (1) said silanol group of said HSE undergoes said condensation reaction with a —COOH group of said first amino acid or peptide to form a Si—O—CO— linkage therewith and (2) thereafter, said second amino acid or peptide undergoes said condensation reaction with said HSE at said Si—O—CO— linkage via a —NH$_2$ group to form said peptide linkage in said polypeptide.

5. The method of claim 4 wherein said condensation reaction of said silanol group of said HSE with a —COOH group of said first amino acid or peptide comprises:

(a) a first reaction of said —COOH group with said silanol and surrounding silanol groups to said HSE to form a hydrogen bonded intermediate;

(b) a second reaction wherein said —COOH group reacts with said silanol group in said hydrogen bonded intermediate to form said Si—O—CO— linkage in a metastable intermediate wherein the silicon atom in said Si—O—CO— linkage is in a penta-coordinate transition state; and (c) a final reaction wherein said metastable intermediate loses a molecule of water resulting in a conversion of said silicon atom from a penta-coordinate transition state to a stable tetra-coordinate state.

6. The method of claim 5 wherein said HSE is a cyclopolysiloxane and said hydrogen bonded intermediate and said metastable intermediate are cyclopolysiloxane derivatives and said third reaction (c) results in a ring opening of said cyclopolysiloxane to form a linear polysiloxane containing said Si—O—CO— linkage.

7. The method of claim 6 wherein said cyclopolysiloxane is selected from the group consisting of cyclodisiloxane, cyclotrisiloxane, cyclotetrasiloxane, cyclopentasiloxane, cyclohexasiloxane, cycloseptasiloxane and cyclooctasiloxane.

8. The method of claim 1 wherein (1) said silanol group of said HSE undergoes said condensation reaction with a —NH$_2$ group of said first amino acid or peptide to form a Si—N—C— linkage therewith and (2) thereafter, said second amino acid or peptide undergoes said condensation reaction with said HSE at said Si—N—C— linkage via a —COOH group to form said peptide linkage in said polypeptide.

9. The method of claim 8 wherein said condensation reaction of said silanol group of said HSE with a —NH$_2$ group of said first amino acid or peptide comprises:

(a) a first reaction of said —NH$_2$ group with said silanol and surrounding silanol groups of said HSE to form a hydrogen bonded intermediate;

(b) a second reaction wherein said —NH$_2$ group reacts with said silanol group in said hydrogen bonded intermediate to form said Si—N—C— linkage in a metastable intermediate wherein the silicon atom in said Si—N—C— linkage is in a penta-coordinate transition state; and (c) a final reaction wherein said metastable intermediate loses a molecule of water resulting in a conversion of said silicon atom from a penta-coordinate transition state to a stable tetra-coordinate state.

10. The method of claim 9 wherein said HSE is a cyclopolysiloxane and said hydrogen bonded intermediate and said metastable intermediate are cyclopolysiloxane derivatives and said third reaction (c) results in a ring opening of said cyclopolysiloxane to form a linear polysiloxane containing said Si—N—C— linkage.

11. The method of claim 10 wherein said cyclopolysiloxane is selected from the group consisting of cyclodisiloxane, cyclotrisiloxane, cyclotetrasiloxane, cyclopentasiloxane, cyclohexasiloxane, cycloseptasiloxane and cyclooctasiloxane.

12. The method of claim 1 including recovering said polypeptide from said reaction medium.

13. The method of claim 1 wherein said first and second amino acids are selected from the group consisting of alanine, glycine, arginine, asparagine, aspartic acid, cysteine, glutamic acid, glutamine, histidine, isoleucine, leucine, lysine, methionine, phenylalanine, proline, serine, threonine, tryptophan, tyrosine and valine.

14. The method of claim 1 conducted in the presence of ultraviolet or visible irradiation.

15. A reaction medium for synthesizing polypeptides comprising an aqueous reaction medium containing a first amino acid or peptide, a second amino acid or peptide and a hydrated silica entity containing silanol groups comprising a cyclopolysiloxane.

16. The reaction medium of claim 15 wherein said cyclopolysiloxane is selected from the group consisting of cyclodisiloxane, cyclotrisiloxane, cyclotetrasiloxane, cyclopentasiloxane, cyclohexasiloxane, cycloseptasiloxane and cyclooctasiloxane.

17. A reaction medium in kit form suitable for admixing to synthesize polypeptides comprising, separately, (1) silica which, when admixed with water, is at least partly converted to a hydrated silica entity containing silanol groups, (2) a first amino acid or peptide and (3) a second amino acid or peptide.

18. The reaction medium in kit form according to claim 17 wherein said (1), (2) and (3) are dissolved or suspended in at least two different aqueous media adapted for admixture with each other to form said reaction medium.

* * * * *